United States Patent [19]

Fung et al.

[11] Patent Number: 5,641,472

[45] Date of Patent: Jun. 24, 1997

[54] TUNGSTEN CLUSTERS

[76] Inventors: Ella Y. Fung, 12499 Lyric Dr. #207;
Stephen R. Cooper, 2020 Lachelle,
both of St. Louis, Mo. 63146

[21] Appl. No.: 504,728

[22] Filed: Jul. 20, 1995

[51] Int. Cl.$^6$ .............................. A61K 49/04; C07F 11/00
[52] U.S. Cl. ........................... 424/9.42; 556/57; 436/173
[58] Field of Search .................................. 556/57; 424/9,
424/9.42; 436/173

[56] References Cited

PUBLICATIONS

Colton et al., Inorganic Chemistry, vol. 23, No. 26, pp. 4738–4742 (1984).

Colton et al., Inorganic Chemistry, vol. 23, No. 24, pp. 4033–4038 (1984).

Powell et al., Inorganic Chemistry, vol. 32, No. 19, pp. 4021–4029 (1993).

*Primary Examiner*—Porfirio Nazario-Gonzalez
*Attorney, Agent, or Firm*—Brian K. Stierwalt

[57] ABSTRACT

The present invention provides new tri-tungsten compounds of the general structure:

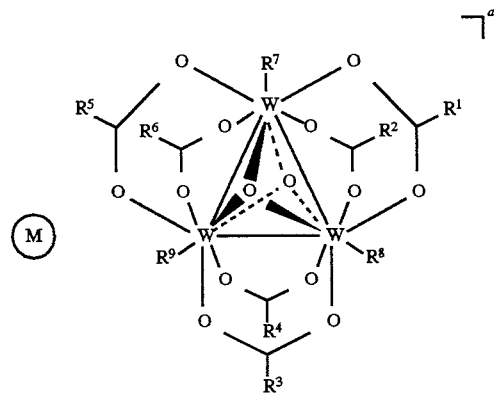

wherein $R^1$ is $-C_kH_lZ_m$ or $-(C_kH_lZ_n)(C_6H_{(5-q)}Z_q)_p$; $R^2$ is $-C_kH_lZ_m$ or $-(C_kH_lZ_n)(C_6H_{(5-q)}Z_q)_p$; $R^3$ is $-C_kH_lZ_m$ or $-(C_kH_lZ_n)(C_6H_{(5-q)}Z_q)_p$; $R^4$ is $-(C_kH_lZ_m)$ or $-(C_kH_lZ_n)(C_6H_{(5-q)}Z_q)_p$; $R^5$ is $-C_kH_lZ_m$ or $-(C_kH_lZ_n)(C_6H_{(5-q)}Z_q)_p$; $R^6$ is $-C_kH_lZ_m$ or $-(C_kH_lZ_n)(C_6H_{(5-q)}Z_q)_p$; Z is a functional group attachable on aliphatic chains or aromatic rings; $R^7$ is an anionic molecule, neutral molecule, $-C_kH_lZ_m$ or $-(C_kH_lZ_n)(C_6H_{(5-q)}Z_q)_p$; $R^8$ is an anionic molecule, neutral molecule, $-C_kH_lZ_m$ or $-(C_kH_lZ_n)(C_6H_{(5-q)}Z_q)_p$; $R^9$ is an anionic molecule, neutral molecule, $-C_kH_lZ_m$ or $-(C_kH_lZ_n)(C_6H_{(5-q)}Z_q)_p$; k is about 0–20; l is about 0–50; m is about 1–50; n is about 0–50; p is about 1–10; q is about 1–5; M is a counter positive or negative ion; and a is about –6–+6. W in the structure is the generally accepted one letter symbol for tungsten. Methods of imaging using compounds of the invention and processes for producing compounds of the invention are also disclosed.

28 Claims, No Drawings

TUNGSTEN CLUSTERS

FIELD OF THE INVENTION

The invention is in the field of imaging. In particular, the invention is in the field of X-ray imaging.

BACKGROUND OF THE INVENTION

Synthesis and characterization of bi-oxo capped trinuclear clusters with the general formula $[M_3(\mu_3\text{-O})_2(O_2CR)_6L_3]^{n\pm}$ (M=Mo, W) are well established. See for example Bino, A.; Ardon, M.; Maor, I.; Kaftory, M.; Dori, Z. *J. Am. Chem. Soc.* 1976, 98, 7093; Bino, A.; Cotton, F. A.; Dori, Z. *J Am. Chem. Soc.* 1978, 100, 5252; Bino, A.; Cotton, F. A.; Dori, Z.; Koch, S.; Kueppers, H.; Millar, M.; Sekutowski, J. *Inorg. Chem.* 1978, 17, 3245; Birnbaum, A.; Cotton, F. A.; Dori, Z.; Reisner, G. M.; Schwotzer, W.; Shaia, M. *Inorg. Chem.* 1983, 22, 2723; Cotton, F. A.; Dori, Z.; Marler, D. O.; Schwotzer, W. *Inorg. Chem.* 1983, 22, 3104; Birnbaum, A.; Cotton, F. A.; Dori, Z.; Kapon, M. *Inorg. Chem.* 1984, 23, 1617; and Cotton, F. A.; Dori, Z.; Marler, D. O.; Schwotzer, W. *Inorg. Chem.* 1984, 23, 4033. This type of cluster contains two capping oxygen atoms sitting above and below the $M_3$ triangular plane. Each metal-metal bond is bridged by two carboxylate groups, leaving the equatorial position, L, at each metal atom occupied by either water, carboxylate or solvent group. These compounds are mainly prepared from refluxing $M(CO)_6$ in carboxylic acid/anhydride mixtures or reducing $M_4{}^{2-}$ under similar reaction conditions. In cases with bulky carboxylate ligands, the assembly of these compounds usually requires high temperature and pressure to yield enough material for characterization. Since the discovery of this class of cluster compounds, most efforts have been directed to the synthesis and characterization of various trinuclear cluster types (see review in Muller, A.; Jostes, R.; Cotton, F. A. *Angew. Chem. Int. Ed. Engl.* 1980, 19, 875; Cotton, F. A. *Polyhedron*, 1986, 5, 3; Cotton, F. A.; Shang, M.; Sun, Z. S. *Inorg. Chim. Acta.* 1993, 212, 95 and references therein). These studies have demonstrated a wide range of $M_3$ clusters with various bridging and capping ligands (Bino, A.; Cotton, F. A.; Dori, Z.; Kolthammer, B. W. S. *J. Am. Chem. Soc.* 1981, 103, 5779; Ardon, M.; Bino, A.; Cotton, F. A.; Dori, Z.; Kaftory, M.; Kolthammer, B. W. S.; Kapon, M.; Reisner, G. M. *Inorg. Chem.* 1981, 20, 4083; Cotton, F. A.; Dori, Z.; Kapon, M.; Marler, D. 0.; Reisner, G. M.; Schwotzer, W.; Shaia, M. *Inorg. Chem..* 1985, 24, 4381; Cotton, F. A.; Felthouse, T. R.; Lay, D. G. *Inorg. Chem.* 1981, 20, 2219; Cotton, F. A.; Shang, M.; Sun, Z. S. *J. Am. Chem. Soc.* 1991, 113, 3007; and Cotton, F. A.; Shang, M.; Sun, Z. S. J. *Cluster Sci.* 1992, 3, 123). Relatively little is known about the reactivity of bi-oxo capped clusters, $[M_3(\mu_3O)_2(O_2CR)_6L_3]^{n\pm}$ (M=Mo, W), partly due to their remarkable stability demonstrated by Cotton and co-workers (see Cotton, F. A.; Dori, Z.; Marler, D. O.; Schwotzer, W. *Inorg. Chem.* 1984, 23, 4033-8). Recently Sasaki and Richens have independently studied the kinetics of terminal water exchange in $[M_3(\mu_3\text{-O})_2(O_2CCH_3)_6(H_2O)_3]^{2+}$ (M=Mo, W) (Nakata, K.; Nagasawa, A.; Soyama, N.; Sasaki, Y.; Ito, T. *Inorg. Chem.* 1991, 30, 1575–9. Powell, G.; Richens, D. T. *Inorg. Chem.* 1993, 32, 4021). Their results show that the water exchange rate in this system is several orders of magnitude slower than in "$M_3(IV)$ aquo ion", $[M_3(\mu_3\text{-O})(\mu\text{-O})_3(H_2O)_9]^{4+}$ (M=Mo, W), and that the degree of inertness is more profound in tungsten case.

Although exchange of the bridging carboxylates has been performed on reactive molybdenum di- and tri-nuclear systems (Telser, j.; Drago, R. S. *Inorg. Chem.* 1984, 23, 1978; Nakata, K.; Yamaguchi, T.; Sasak, Y.; Ito, T. *Chem. Lett.* 1992. 6, 983–6), no such direct carboxylate exchange has been successfully performed on the bi-oxo capped $W_3$ system, $[W_3(\mu_3\text{-O})_2(O_2CR)_6L_3]^{n\pm}$.

SUMMARY OF THE INVENTION

The present invention describes a new process that incorporates functionalized ligands onto tri-tungsten clusters to form new compounds. These new clusters possess desirable properties such as radiopacity and solubility, and they can also be modified with heavy elements to form highly radiopaque materials for use in diagnostic X-ray imaging.

The present invention provides new tri-tungsten compounds of the general structure:

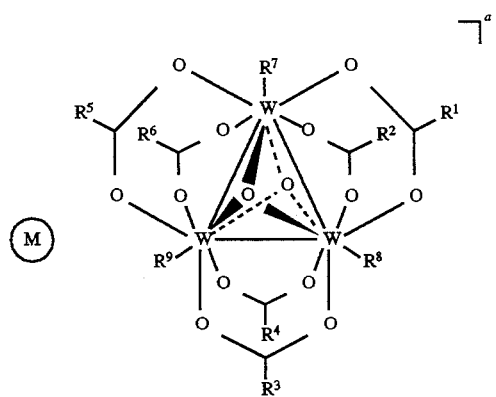

wherein $R^1$ is $—C_kH_1Z_m$ or $—(C_kH_1Z_n)(C_6H_{(5-q)}Z_q)_p$; $R^2$ is $—C_kH_1Z_m$ or $—(C_kH_1Z_n)(C_6H_{(5-q)}Z_q)_p$; $R^3$ is $—C_kH_1Z_m$ or $—(C_kH_1Z_n)(C_6H_{(5-q)}Z_q)_p$; $R^4$ is $—(C_kH_1Z_m)$ or $—(C_kH_1Z_n)(C_6H_{(5-q)}Z_q)_p$; $R^5$ is $—C_kH_1Z_m$ or $—(C_kH_1Z_n)(C_6H_{(5-q)}Z_q)_p$; $R^6$ is $—C_kH_1Z_m$ or $—(C_kH_1Z_n)(C_6H_{(5-q)}Z_q)_p$; Z is a functional group attachable on aliphatic chains or aromatic rings; $R^7$ is an anionic molecule, neutral molecule, $—C_kH_1Z_m$ or $—(C_kH_1Z_n)(C_6H_{(5-q)}Z_q)_p$; $R^8$ is an anionic molecule, neutral molecule, $—C_kH_1Z_m$ or $—(C_kH_1Z_n)(C_6H_{(5-q)}Z_q)_p$; $R^9$ is an anionic molecule, neutral molecule, $—C_kH_1Z_m$ or $—(C_kH_1Z_n)(C_6H_{(5-q)}Z_q)_p$; k is about 0–20; l is about 0–50; m is about 1–50; n is about 0–50; p is about 1–10; q is about 1–5; M is a counter positive or negative ion; and a is about −6–+6. W in the structure is the generally accepted one letter symbol for tungsten.

A process for producing compounds of the general formula:

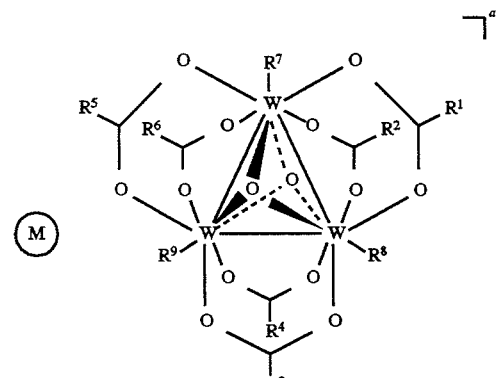

wherein $R^1$ is $—C_kH_1Z_m$ or $—(C_kH_1Z_n)(C_6H_{(5-q)}Z_q)_p$; $R^2$ is $—C_kH_1Z_m$ or $—(C_kH_1Z_n)(C_6H_{(5-q)}Z_q)_p$; $R^3$ is $—C_kH_1Z_m$ or —$(C_kH_1Z_n)$ $(C_6H_{(5-q)} Z_q)_p$; $R^4$ is —$(C_kH_1Z_m)$ or —$(C_kH_1Z_n)$ $(C_6H_{(5-q)} Z_q)_p$; $R^5$ is —$C_kH_1Z_m$ or —$(C_kH_1Z_n)$ $(C_6H_{(5-q)} Z_q)_p$; $R^6$ is —$C_kH_1Z_m$ or —$(C_kH_1Z_n)$ $(C_6H_{(5-q)} Z_q)_p$; Z is a functional group attachable on aliphatic chains or aromatic rings; $R^7$ is an anionic molecule, neutral molecule, —$C_kH_1Z_m$ or —$(C_kH_1Z_n)$ $(C_6H_{(5-q)} Z_q)_p$; $R^8$ is an anionic molecule, neutral molecule, —$C_kH_1Z_m$ or —$(C_kH_1Z_n)$ $(C_6H_{(5-q)} Z_q)_p$; $R^9$ is an anionic molecule, neutral molecule, —$C_kH_1Z_m$ or —$(C_kH_1Z_n)$ $(C_6H_{(5-q)} Z_q)_p$; k is about 0–20; l is about 0–50; m is about 1–50; n is about 0–50; p is about 1–10; q is about 1–5; M is a counter positive negative ion; and a is about −6–+6; comprising heating bioxo capped tri-tungsten clusters in the presence of a ligand, provided the ligand is in excess of the tri-tungsten cluster, and recovering a fully or partially substituted tri-tungsten cluster.

Also, methods of imaging using compounds of the invention are disclosed.

DETAILED DESCRIPTION OF THE INVENTION

General procedures for preparing tri-nuclear tungsten clusters include Cotton, F. A.; Wilkinson, G. *Advance Inorganic Chemistry*; 4th Ed.; John Wiley & Son: New York, 1980, pp. 868–871; Cotton, F. A. *Polyhedron*, 1986, 5,5; Bino, A.; Ardon, M.; Maor, I.; Kaforty, M.; Dori, Z. *J. Am. Chem. Soc.* 1976, 98, 7093; Bino, A.; Cotton, F. A.; Dori, Z. *J Am. Chem. Soc.* 1978, 100, 5252. Bino, A.; Cotton, F. A.; Dori, Z.; Koch, S.; Kueppers, H.; Millar, M.; Sekutowski, J. *Inorg. Chem.* 1978, 17, 3245. Birnbaum, A.; Cotton, F. A.; Dori, Z.; Reisner, G. M.; Schwotzer, W.; Shaia, M. *Inorg. Chem.* 1983, 22, 2723. Cotton, F. A.; Dori, Z.; Marler, D. O.; Schwotzer, W. *Inorg. Chem.* 1983, 22, 3104 and Cotton, F. A.; Dori, Z.; Marler, D. O.; Schwotzer, W. *Inorg. Chem.* 1984, 23, 4033. Typically tungsten clusters are prepared from refluxing tungsten hexacarbonyl or sodium tungstate/zinc in carboxylic acid/anhydride mixtures. In cases with bulky carboxylate ligands, it usually requires high temperature or high boiling solvents and high pressure to yield enough material for characterization. To date, however, no functionalized carboxylate groups have been used to successfully assemble the $W_3(\mu_3-O)_2(O_2CR)_6$ unit, due to the lack of commercially available anhydrides and to intractable side reactions during the course of cluster assembly. By using the assembled $W_3(\mu_3-O)_2$ unit in the parent cluster as a template, ligand exchange in this system offers a facile synthetic route to new $W_3$ clusters that cannot be prepared by prior art. Compounds of the invention are therefore prepared after the parent tungsten cluster is obtained and the process of the invention is applied.

The process of the invention comprises heating a parent tri-tungsten cluster in the presence of a desired ligand, and a new tri-tungsten cluster substituted with desired ligand is obtained. Heating temperatures typically range from about 80° C. to about 160° C. Generally the heating time is from about 2 to 5 hours, mostly depending on the ligand. Recovery of desired cluster is obtained by conventional chromatographic methods. As long as there is excess ligand over the tungsten cluster, there will be fully or partially substituted clusters obtained. Preferably, 10% or more excess ligand is used. Any bi-oxo capped tri-tungsten cluster can be used in the process of the invention. Suitable ligands for use in the process of the invention include bidentate ligands and multidentate ligands, such as carboxylate ligands, oxylate ligands, phosphate ligands, and sulfonate ligands. The process of the invention provides high yields. Yields from the process of the invention are especially high in view of yields obtained for known compounds with prior art processes that require heating W(W)6 or $[WO_4]^{2+}/Z_n$ in desired carboxylic acid anhydride at high temperatures (137° C.–160° C.) and high pressure. High temperatures and pressure may contribute to decomposition of the cluster and give intractable side products that lead to corresponding lower yield.

Functional groups for use with the invention include acids, acyl halides, alcohols, aldehydes, alkoxides, alkenes, alkynes, amides, amines, amino acids, aryl halides, carbohydrates, carboxylates, esters, ethers, ketones, isocyanates, hydroxides, phosphates, phosphonates, sulfates, sulfonates and halogens (F, Cl, Br, I). Functional groups also include any iodinated substituents that improve the overall radio-opacity of the compound. Any unit of two or more atoms that are joined together to give a net charge of zero can serve as the neutral molecule. Neutral molecule groups for use with the invention include water, carbohydrates, organic solvents, and alcohols. Neutral molecules and anionic species are generally used to alter the overall charge of the tungsten cluster. Anionic species such as alkoxides, carboxylates, halides, hydroxides, isocyanates, phosphates, phosphonates, sulfates and sulfonates can also be used in the neutral molecule position to alter the overall charge. Alcohols include branched and unbranched such as methanol, ethanol, propanol and isopropanol. Halogens include fluorine, chlorine, bromine, and iodine. Aldehydes include methyl aidehyde, benzyl aidehyde, and phenyl acetaldehyde. Alkenes include ethene, propene, butene and acrylic. Alkoxides include methoxide, ethoxide, phenoxide and glycerides. Alkynes include ethyne, propyne, butyne and pentyne. Amides include acetamide and benzamide. Amines include primary, secondary, and tertiary amines. Aryl halides include fluorine, chlorine, bromine and iodine substituted aromatic rings. Carbohydrates include glucose and fructose. Esters include alkyl, phenyl and benzyl esters. Ketones include alkyl, phenyl and benzyl ketones. Organic polar or non-polar solvents include acetone, acetonitrile, benzene, dichloromethane, diethyl ether, diglyme, dimethyl acetamide, dimethyl formamide, dimethyl sulfoxide, nitromethane, nitrobenzene, pyridine, tetrahydrofuran, and toluene. Carboxylates include acetate, acrylate, butyrate, propionate, benzoate, and phenyl acetate. Counter ions include Group I, II and VII ions, typically sodium, potassium, cesium, magnesium, calcium, barium, chloride, bromide and iodide ions. Counter ions also include any other cationic or anionic species such as ammoniums, arsoniums, carbonates, carboxylates, nitrates, phosphates, phosphoniums, polytungstates, sulphates. The overall charge of the molecule ranges from −6 to +6, typically −1 to about +2.

Examples of compounds of the invention include:

Sodium triangulo hexakis[μ-(acetato-O:OÕ)]tris(acetato-O)di-$\mu_3$-oxotritungsten(IV);

Sodium triangulo hexakis[μ-(propinato-O:OÕ)]tris(propionato-O)di-$\mu_3$-oxotritungsten(IV);

Sodium triangulo hexakis[μ-(methoxyacetato-O:OÕ)]tris(methoxyacetato-O)di-$\mu_3$-oxotritungsten(IV);

Sodium triangulo hexakis[μ-(acrylato-O:OÕ)]tris(acrylato-O)di-$\mu_3$-oxotritungsten(IV);

Sodium triangulo hexakis[μ-(benzoato-O:OÕ)]tris(benzoato-O)di-$\mu_3$-oxotritungsten(IV);

Sodium triangulo hexakis[μ-(phenylacetato-O:OÕ)]tris(phenylacetato-O)di-$\mu_3$-oxotritungsten(IV);

Sodium triangulo hexakis[μ-(p-hydoxyphenylacetato-O:OÕ)]tris(p-hydoxyphenylacetato-O)di-$\mu_3$-oxotritungsten(IV);

Sodium triangulo hexakis[μ-(4-acetoxyglycolamido-3,5-diiodophenylacetato-O:OÕ)]tris(4-acetoxyglycolamido-3,5-diiodophenylacetato-O)di-μ$_3$-oxotritungsten(IV);

Sodium triangulo hexakis[μ-(pyruvato-O:OÕ)]tris(pyruvato-O)di-μ$_3$-oxotritungsten(IV);

Sodium triangulo hexakis[μ-(DL-lactato-O:OÕ)]tris(DL-lactato-O)di-μ$_3$-oxotritungsten(IV);

Sodium triangulo hexakis[μ-(glycolato-O:OÕ)]tris(glycolato-O)di-μ$_3$-oxotritungsten(IV);

Sodium triangulo hexakis[μ-(glycerato-O:OÕ)]tris(glycerato-O)di-μ$_3$-oxotritungsten(IV);

Triangulo monoaquohexakis[μ-(acetato-O:OÕ)](dihydroxy-O)di-μ$_3$-oxotritungsten (IV);

Triangulo monoaquohexakis[μ-(propionato-O:OÕ)](dihydroxy-O)di-μ$_3$-oxotritungsten (IV);

Triangulo monoaquohexakis[μ-(methoxyacetato-O:OÕ)](dihydroxy-O)di-μ$_3$-oxotritungsten (IV);

Triangulo monoaquohexakis[μ-(acrylato-O:OÕ)](dihydroxy-O)di-μ$_3$-oxotritungsten (IV);

Triangulo monoaquohexakis[μ-(benzoato-O:OÕ)](dihydroxy-O)di-μ$_3$-oxotritungsten (IV);

Triangulo monoaquohexakis[μ-(phenylacetato-O:OÕ)](dihydroxy-O)di-μ$_3$-oxotritungsten (IV);

Triangulo monoaquohexakis[μ-(p-hydroxyphenylacetato-O:OÕ)](dihydroxy-O)di-μ$_3$-oxotritungsten (IV);

Triangulo monoaquohexakis[μ-(4-acetoxyglycolamido-3,5-diiodophenylacetatato-O:OÕ)](dihydroxy-O)di-μ$_3$-oxotritungsten (IV);

Triangulo monoaquohexakis[μ-(pyruvato-O:OÕ)](dihydroxy-O)di-μ$_3$-oxotritungsten (IV);

Triangulo monoaquohexakis[μ-(DL-lactato-O:OÕ)](dihydroxy-O)di-μ$_3$-oxotritungsten (IV);

Triangulo monoaquohexakis[μ-(glycolato-O:OÕ)](dihydroxy-O)di-μ$_3$-oxotritungsten(IV);

Triangulo monoaquohexakis[μ-(glycerato-O:OÕ)](dihydroxy-O)di-μ$_3$-oxotritungsten(IV);

Triangulo diaquohexakis[μ-(acetato-O:OÕ)](hydroxy-O)di-μ$_3$-oxotritungsten(IV)chloride;

Triangulo diaquohexakis[μ-(propinato-O:OÕ)](hydroxy-O)di-μ$_3$-oxotritungsten(IV)chloride;

Triangulo diaquohexakis[μ-(acrylato-O:OÕ)](hydroxy-O)di-μ$_3$-oxotritungsten (IV) chloride;

Triangulo diaquohexakis[μ-(methoxyacetato-O:OÕ)](hydroxy-O) di-μ$_3$-oxotritungsten(IV)chloride;

Triangulo diaquohexakis[μ-(benzoato-O:OÕ)](hydroxy-O)di-μ$_3$-oxotritungsten(IV)chloride;

Triangulo diaquohexakis[μ-(phenylacetato-O:OÕ)](hydroxy-O) di-μ$_3$-oxotritungsten(IV)chloride;

Triangulo diaquohexakis[μ-(4-acetoxyglycolamido-3,5-diiodophenylacetato-O:OÕ)](hydroxy-O)di-μ$_3$-oxotritungsten(IV)chloride;

Triangulo diaquohexakis [μ-(p-hydroxyphenylacetato-O:OÕ)](hydroxy-O)di-μ$_3$-oxotritungsten (IV) chloride;

Triangulo diaquohexakis[μ-(pyruvato-O:OÕ)](hydroxy-O)di-μ$_3$-oxotritungsten(IV)chloride;

Triangulo diaquohexakis[μ-(DL-lactato-O:OÕ)](hydroxy-O)di-μ$_3$-oxotritungsten (IV) chloride;

Triangulo diaquohexakis[μ-(glycolato-O:OÕ)](hydroxy-O)di-μ$_3$-oxotritungsten(IV)chloride;

Triangulo diaquohexakis[μ-(glycerato-O:OÕ)](hydroxy-O)di-μ$_3$-oxotritungsten(IV)chloride.

Triangulo triaquohexakis[μ-(acetato-O:OÕ)]di-μ$_3$-oxotritungsten(IV) dichloride;

Triangulo triaquohexakis [μ-(propionato-O:OÕ)]di-μ$_3$-oxotritungsten(IV) dichloride;

Triangulo triaquohexakis[μ-(methoxyacetato-O:OÕ)]di-μ$_3$-oxotritungsten(IV) dichloride;

Triangulo triaquohexakis[μ-(acrylato-O:OÕ)]di-μ$_3$-oxotritungsten(IV) dichloride;

Triangulo triaquohexakis[μ-(benzoato-O:OÕ)]di-μ$_3$-oxotritungsten(IV) dichloride;

Triangulo triaquohexakis[μ-(phenylacetato-O:OÕ)]di-μ$_3$-oxotritungsten(IV) dichloride;

Triangulo triaquohexakis[μ-(p-hydroxyphenylacetato-O:OÕ)]di-μ$_3$-oxotritungsten(IV) dichloride;

Triangulo triaquohexakis[μ-(4-acetoxyglycolamido-3,5-diiodophenylacetato-O:OÕ)]di-μ$_3$-oxotritungsten(IV) dichloride;

Triangulo triaquohexakis [μ-(pyruvato-O:OÕ)]di-μ$_3$-oxotritungsten(IV) dichloride;

Triangulo triaquohexakis[μ-(DL-lactato-O:OÕ)]di-μ$_3$-oxotritungsten(IV) dichloride;

Triangulo triaquohexakis[μ-(glycolato-O:OÕ)]di-μ$_3$-oxotritungsten(IV) dichloride; and Triangulo triaquohexakis [μ-(glycerato-O:OÕ)]di-μ$_3$-oxotritungsten(IV) dichloride.

The compositions of the invention can be formulated into diagnostic compositions for enteral or parenteral administration. These compositions contain an effective amount of the radiopaque ion complex along with conventional pharmaceutical carriers and excipients appropriate for the type of administration contemplated. For example, parenteral formulations advantageously contain a sterile aqueous solution or suspension of from about 0.05 to about 1.0M of a complex according to this invention. Parenteral compositions may be injected directly or mixed with a large volume parenteral composition for systemic administration. Preferred parenteral formulations have a concentration of complex of about 0.1M to about 0.5M. Such solutions also may contain pharmaceutically acceptable buffers and, optionally, electrolytes such as sodium chloride. The compositions may advantageously contain a slight excess (e.g., from about 0.01 to about 15.0 mole % of excess) of a complexing agent or its complex with a physiologically acceptable, non-toxic cation. Such physiologically acceptable, non-toxic cations include calcium ions, magnesium ions, copper ions, zinc ions, salts of n-methylglucamine and diethalanolamine, and the like.

Formulations for enteral administration may vary widely, as is well-known in the art. In general, such formulations are liquids which include an effective amount of the complex in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the image. Such doses may vary widely, depending upon the particular complex employed, the organs or tissues which are the subject of the imaging procedure, the imaging equipment being used, and the like. In general, parenteral dosages will range from about 0.001 to about 1.0 mmol of complex per kg of patient body weight. Preferred parenteral dosages range from about 0.01 to about 0.5 mmol of complex per kg of patient body weight. Enteral dosages generally range from about 0.5 to about 100 mmol, preferably from about 1.0 to about 20 mmol, more preferably from about 1.0 to about 10.0 mmol of complex per kg of patient body weight.

The diagnostic compositions of the invention are used in the conventional manner. The compositions may be administered to a patient, typically a warm-blooded animal, either systematically or locally to the organ or tissue to be imaged, and the patient then subjected to the imaging procedure.

X-ray contrast Imaging Procedures are found in Albert A. Moss, M.D., Gordon Gamsu, M.D., and Harry K. Genant, M.D., *Computed Tomography of the Body*, (W.B. Saunders Company, Philadelphia, Pa. 1992) and M. Sovak, Editor, *Radiocontrast Agents*, (Springer-Verlag, Berlin 1984).

General procedures for ligand synthesis and metal complexing are well known and exemplified in such texts as Watson, A.D., Rocklage, S.C., Carvlin, M.J. In Magnetic Resonance Imaging, 2nd ed.; Stark, D.D., Bradley, W.G., Eds.; Mosby Year Book: St. Louis, Mo. 1992, Chapter 14 and Gaughan, G. In Enhanced Magnetic Resonance Imaging, Runge, V.M., Ed.; Mosby Year Book: St. Louis, Mo., 1989, Chapter 9.

The following examples illustrate the specific embodiments of the invention described in this document. As would be apparent to skilled artisans, various changes and modifications are possible and are contemplated within the scope of the invention described.

EXAMPLES

Synthesis of $Na[W_3(\mu_3-O)_2(O_2CCH_3)_9]$ (1)

$Na[W_3(\mu_3-O)_2(O_2CCH_3)_9]$ (1). A mixture of 5.0 g of $Na_2WO_4$ (15 mmol) and 6.0 g $W(CO)_6$ (17 mmol) was heated in acetic anhydride/acetic acid (1:10, 250 mL) at 140° C. for 10 h. After the reaction mixture had cooled to 70° C., yellow percipitates were filtered and washed successively with acetic anhydride and diethyl ether. It was recrystallized by dissolution in methanol (10 mL/g) and precipitation from acetonitrile (30 mL/g); yield 7.65 g (63%): $^1H$ NMR (300 MHz, DMSO-$d_6$)__$\delta$ 1.98 (s, 9H), 2.24 ppm (s, 18H); UV-vis ($H_2O$)__$\lambda$max ($\epsilon$, $mol^{-1}$ $dm^3$ $cm^{-1}$) 378 (1530), 454 (1620) nm; ESI-MS m/z for $[W_3(\mu_3-O)_2(O_2CCH_3)_9]^-$ is 1114; Analysis calc'd for $Na[W_3(\mu_3-O\ _2(O_2CCH_3)_9]$, $C_{18}H_{27}NaO_{20}W_3$: C, 19.0; H, 2.4; Na, 2.0; W, 48.5; found: C, 18.8; H, 2.7; Na, 2.1; W, 49.8.

EXAMPLE 1

$Na[W_3(\mu_3-O)_2(O_2CCH_2CH_3)_9]$ (2). A solution of $Na[W_3(\mu_3-O)_2(O_2CCH_3)_9]$ (108 mg, 0.095 mmol) in propionic acid (10 mL) was heated to 80° C. for 2 h. The resulting yellow solution was evaporated to dryness to leave a yellow-brown residue. It was disssolved in methanol and purified by passing through a basic alumina column; yield 42 mg (35 %): $^1H$ NMR (300 MHz, DMSO-$d_6$)__$\delta$ 1.03 (m, 27H), 2.27 (q, 6H), 2.46 (q, 12H); $^{13}C$ NMR (75.6 MHz, DMSO-$d_6$)__$\delta$ 11.3, 11.4, 30.0, 32.2, 177.8, 186.2; IR (KBr)__$v$ 2979, 2938, 2881, 1643, 1555, 1470, 1446, 1378, 1235, 1077, 901, 810, 675, 638, 605, 546 $cm^{-1}$; UV-vis (DMSO)__$\lambda$max ($\epsilon$,$mol^{-1}$ $dm^3$ $cm^{-1}$) 386 (2500), 461 (2300) nm; ESI-MS m/z for $[W_3(\mu_3-O)_2(O_2(O_2CCH_2CH_3)_9]^-$ is 1240; Analysis calc'd for $Na[W_3(W_3-O)_2(O_2CCH_2CH_3)_9].3H_2O$, $C_{27}H_{51}NaO_{23}W_3$: C, 24.6; H, 3.9 Na, 1.7; found: C, 24.3; H, 3.6; Na, 2.0.

EXAMPLE 2

$Na[W_3(\mu_3-O)_2(O_2CCH_2CH_2CH_3)_9]$ (3). This compound was prepared similarly to $Na[W_3(\mu_3-O)_2(O_2CCH_2CH_3)_9]$ using excess butyric acid (CAUTION! STENCH!) in place of propionic acid. Pure product was isolated as yellow-brown oil; yield 55.1 mg (45%): $^1H$ NMR ($CD_3OD$)__$\delta$ 0.92 (m, 27H), 1.64 (m, 18H), 2.48 (m, 18H) ppm; $^{13}C$ NMR ($CD_3OD$)__$\delta$ 13.18, 13.79, 19.61, 19.83, 37.91, 41.04, 180.72, 186.34 ppm; IR (KBr)__$v$ 2958, 2926, 2874, 1700, 1642, 1611, 1558, 1447, 1353, 1321, 1211, 1095, 937, 895, 805, 642, 600, 437 $cm^{-1}$; UV-vis (methanol)__$\lambda$max ($\epsilon$,$mol^{-1}$ $dm^3$ $cm^{-1}$) 381 (2100), 458 (2300) nm; ESI-MS m/z for $[W_3(\mu_3-O)_2(O_2CCH_2CH_2CH_3)_9]^-$ is 1368.

EXAMPLE 3

$Na[W_3(\mu_3-O)_2(O_2C(CH_3)_3)_6(OCH_3)_3]$ (4). $Na[W_3(\mu_3-O)_2(O_2CCH_3)_9]$ (100 mg, 0.088 mmol) was added to 10 mL (87.0 mmol) of molten trimethyl acetic acid and slowly heated to 80° C. for 4 h. The resulting yellow-brown material was dissolved in methyl alcohol and passed through a basic alumina column. A yellow band was collected, concentrated, and passed through a second column of basic alumina. On rotary evaporation a yellow crystalline product was obtained; yield 22.8 mg (18%): $^1H$ NMR (300 MHz, $CD_3OD$)__$\delta$ 1.15 (s,54H), 3.34 (s, 9H) ppm; $^{13}C$ NMR ($CD_3OD$)__$\delta$ 27.7 ppm (resonances for the quaternary carbons and coordinated methoxide groups were obscured); IR (KBr)__$v$ 2963, 2928, 2875, 2806, 1555, 1485, 1428, 1381, 1361, 1233, 1069, 909, 809, 780, 627, 599, 465 and 452 $cm^{-1}$; UV-vis (methanol)__$\lambda$max ($\epsilon$,$mol^{-1}$ $dm^3$ $cm^{-1}$) 384 (1700), 458 (2000) nm; ESI-MS m/z for $[W_3(\mu_3-O)_2(O_2CC(CH_3)_3)_6(OCH_3)_3]^-$ is 1284; Analysis calc'd for $Na[W_3(\mu_3-O)_2(O_2CC(CH_3)_3)_6(OCH_3)_3]\cdot 5\ CH_3OH$, $C_{38}H_{83}NaO_{22}W_3$: C, 31.1; H, 5.70; Na, 1.57; found: C, 31.1; H, 5.05; Na, 1.08.

EXAMPLE 4

$Na[W_3(\mu_3-O)_2(O_2CCH=CH_2)_7(O_2CCH_2CH_2CH=CHCOOH)_2]$ (5). A solution of $Na[W_3(\mu_3-O)_2(O_2CCH_3)_9]$ (1) (500 mg, 0.11 mmol) in 50 mL (729 mmol) of acrylic acid was slowly heated to 80° C. for 6 hours. Initial color of the reaction mixture was yellow-brown. After heating to 80° C., color changed to orange with orange precipitate. The orange solution was filtered and orange insoluble material was isolated. Excess acrylic acid in the orange solution was removed by evaporation, from which a crude product was obtained. The pure orange crystalline product was isolated from a chromatotron plate using 10%, 15% and 25% of methanol in ethyl acetate as an eluate; yield 32.3 mg (5.5%): $^1H$ NMR (300 MHz, $CD_3OD$) __$\delta$ centered at 2.82 (t), 4.52 (t), 5.84 (m) and 6.27 (m) ppm; $^{13}C$ NMR (75.6 MHz, $CD_3OD$)__$\delta$ 128.5, 128.9, 130.7, 32.2, 176.3, 178.4 ppm; IR (KBr)__$v$ 1723, 1636, 1541, 1444, 1405, 1376, 1344, 1278, 1190, 1058, 984, 812, 694, 667, 635, 601 $cm^{-1}$; UV-vis (methanol)__$\lambda$max ($\epsilon$,$mol^{-1}$ $dm^3$ $cm^{-1}$) 333 (11,000), 367 (6100) and 481 (4000) nm; ESI-MS m/z for $[W_3(\mu_3-O)_2(O_2CCH=CH_2)_7(O_2CCH_2CH_2CH=CHCOOH)_2]^-$ is 1368; Analysis calc'd for $Na[W_3(\mu_3-O)_2(O_2CCH=CH_2)_7(O_2CCH_2CH_2CH=CHCOOH)_2]$, $C_{33}H_{35}NaO_{24}W_3$: C, 28.51; H, 2.54; Na, 1.65; found: C, 28.12; H, 2.64; Na, 1.35.

EXAMPLE 5

$[W_3(\mu_3-O)_2(O_2CCH=CH_2)_6(H_2O)_3]Cl_2$ (6). Hydrolysis of crude $W_3$-acrylate cluster (5) (456 mg) by heating in 36% HCl at room temperature for three days yielded orange solution and unreacted starting material. The orange solution was filtered and slow evaporation yielded orange crystals, yield 170 mg (44.8%): $^1H$ NMR (300 MHz, $CD_3OD$)__$\delta$ centered at 5.85 (d), 6.26 (m), 6.48 (d) ppm; $^-C$ NMR (75.6

MHz, CD$_3$OD)_δ 128.6, 132.6, 178.6 ppm; IR (KBr)_ν 2953, 1642, 1526, 1447, 1379, 1279, 1068, 984, 816, 700, 647, 605, 437 cm$^{-1}$; UV-vis (methanol)_λmax (ε,mol$^{-1}$ dm$^3$ cm$^{-1}$) 324 (11,000), 362 (shoulder, 6500), 473 (5400) ESI-MS m/z for [W$_3$(μ$_3$-O)$_2$(O$_2$CCH=CH$_2$)$_6$(H$_2$O)$_3$]$^{2+}$ is 532.

EXAMPLE 6

Na[W$_3$(μ$_3$-O)$_2$(O$_2$CCH$_2$OCH$_3$)$_9$] (7). A solution of 2.28 g (2 mmol) of Na[W$_3$(μ$_3$-O)$_2$(O$_2$CCH$_3$)$_9$] (1) in 3.6 g (40 mmol) of methoxyacetic acid containing a few drops of methoxyacetic anhydride was heated at 130° C. for 3 hours under nitrogen. Any volatiles were removed by gradual application of vacuum at 100°–130° C. The residue was treated with another 3.6 g portion of methoxyacetic acid, and the same procedure was repeated. After thorough removal of all volatiles under high vacuum at 130° C., the residue was cooled and dissolved in 10 mL of acetonitrile. Upon standing, yellow-brown crystals of the product was separated, yield 1.97 g (70%): $^1$H NMR (300 MHz, CD$_3$OD) _δ 3.40 (s, 18H), 3.43 (s, 9H), 4.20 (s, 6H), 4.34 (s, 12H); UV-vis (H$_2$O)_λmax (ε,mol$^{-1}$ dm$^3$ cm$^{-1}$) 380 (1550) and 454 (1660) nm; ESI-MS m/z for [W$_3$(μ$_3$-O)$_2$(O$_2$CCH$_2$OCH$_3$)$_9$]$^-$ is 1383; Analysis calc'd for Na[W$_3$(μ$_3$-O)$_2$(O$_2$CCH$_2$OCH$_3$)$_9$]. 1.5 MeCN, C$_{30}$H$_{49.5}$N$_{1.5}$NaO$_{29}$W$_3$: C, 24.5; H 3.4; N, 1.4; Na, 1.6; W, 37.5; found: C, 24.3; H, 3.5; N, 1.3; Na, 1.6; W, 32.1.

EXAMPLE 7

Na[W$_3$(μ$_3$-O)$_2$(O$_2$CCH$_2$C$_6$H$_5$)$_9$] (8). A mixture of Na [W$_3$(μ$_3$-O)$_2$(O$_2$CCH$_3$)$_9$] (1 g, 0.9 mmol) and phenylacetic acid (10 g, 73 mmol) was stirred at 100° C. for 5 h. It was then subjected to column chromatography (0–25% acetonitrile in methylene chloride) over silica gel to give a yellow product yield 0.61 g (38%): $^1$H NMR (300 MHz, DMSO-d$_6$)_δ 3.18 (s, 6H), 3.70 (s, 12H), 7.0–7.2 (m, 45H) ppm; $^{13}$C NMR (75.6 MHz, DMSO-d$_6$)_δ 41.5, 44.6, 125.6, 126.8, 127.8, 128.4, 129.1, 129.9, 135.1, 138.2, 174.0, 182.7; IR (KBr)_ν 1625, 1547, 1481, 1425, 1327, 1266, 1198, 1145, 711, 677, 648, 612, 581 cm$^{-1}$; UV-vis (methanol)_λ$_{max}$ (ε, mol$^{-1}$ dm$^3$cm$^{-1}$) 284 (16,400), 382 (2030), 459 (2045) nm; ESI-MS m/z for [W$_3$(μ$_3$-O)$_2$(O$_2$CCH$_2$C$_6$H$_5$)$_9$]$^-$ is 1799; Analysis calc'd for Na[W$_3$(μ$_3$-O)$_2$(O$_2$CCH$_2$C$_6$H$_5$)$_9$], C$_{72}$H$_{63}$NaO$_{20}$W$_3$: C, 47.4; H 3.48; Na, 1.26; found: C, 49.71; H, 4.51; Na, 1.17.

EXAMPLE 8

[W$_3$(μ$_3$-O)$_2$(O$_2$CCH$_2$C$_6$H$_5$OH)$_6$(MeOH)$_3$]Cl$_2$ (9). A mixture of Na[W$_3$(μ$_3$-O)$_2$ (O$_2$CCH$_3$)$_9$] (5 g, 4.3 mmol) and p-hydroxyphenylacetic acid (18 g, 118 mmol) was stirred at 165° C. for 5 h. The solid mass, obtained after cooling to room temperature, was triturated with diethyl ether to extract excess p-hydroxyphenylacetic acid. The residue was dissolved in methanol (500 mL), bubbled with HCl, and stirred at ambient temperature for three days. The resulting solution was then evaporated to dryness and the residue was purified by column chromatography (conc.HCl(aq):MeOH:MeCN, 0:25:75 to 0.5:99.5:0) to give a yellow solid; yield 1.2 g (16%): $^1$H NMR (300 MHz, DMSO-d$_6$)_δ 3.69 (m, 12H), 6.7 (m, 12H), 6.9 (m, 12H) ppm; $^{13}$C NMR (75.6 MHz, DMSO-d$_6$)_δ 40.9, 115.4, 124.6, 130.1, 156.7, 185.4 ppm; IR (KBr)_ν 3432, 2960, 2925, 1615, 1552, 1516, 1437, 1239, 1174, 803,741, 704, 647 cm$^{-1}$; UV-vis (methanol)_ λmax (ε, mol$^{-1}$ dm$^3$cm$^{-1}$) 278 (6200), 378 (550), 460 (664) nm; ESI-MS m/z for [M-H]$^+$, where [M-H]$^+$=[W$_3$(μ$_3$-O)$_2$(O$_2$CCH$_2$C$_6$H$_4$OH)$_6$(MeOH)$_2$(OMe)]$^+$, is 1586 and signals observed at 1555 and 1523 are due to successive loss of methanol; Analysis calc'd for [W$_3$(μ$_3$-O)$_2$(O$_2$CCH$_2$C$_6$H$_4$OH)$_6$(MeOH)$_3$]Cl$_2$, C$_{51}$H$_{54}$Cl$_2$O$_{23}$W$_3$: C, 36.96; H, 3.28; Cl, 4.28; found: C, 35.76; H, 3.39; Cl, 4.21.

EXAMPLE 9

[W$_3$(μ$_3$-O)$_2$(O$_2$CCHOHCH$_3$)$_6$(H$_2$O)$_3$]Cl$_2$ (10). A mixture of Na[W$_3$(μ$_3$-O)$_2$(O$_2$CCH$_3$)$_9$] (5 g, 4.3 mmol) in 109 mL of DL-lactic acid (85% in H$_2$O) was heated at 130° C. for 20 h. Excess lactic acid and side products were removed by vacuum distillation at 110° C. The resulting crude product was recrystallized from methanol/ethyl ether. This material was further treated with another portion of DL-lactic acid, and the same procedure was repeated. After thorough removal of all volatiles under high vacuum at 110° C., Na[W$_3$(μ$_3$-O)$_2$(O$_2$CCHOHCH$_3$)$_9$] was purified by dissolution in methanol and precipitation from ethyl ether, yield 7.5 g. A solution of 1.0 g (0.71 mmol) of Na[W$_3$(μ$_3$-O)$_2$(O$_2$CCHOHCH$_3$)$_9$] was stirred in 40 mL of 1M HCl at room temperature for 2 d. The resulting reaction solution was evaporated down to ~2 mL and precipitated from acetone. A 350 mg portion of this material was purified by ion-exchange column chromatography (Dowex 50×2-200), yield 200 mg (64.5% based on W$_3$): $^1$H NMR (300 MHz, CD$_3$OD)_δ 1.39 (m,18H), 4.60 (q, 6H); ESI-MS m/z for [W$_3$(μ$_3$-O)$_2$(O$_2$CCHOHCH$_3$)$_6$(H$_2$O)$_3$]$^{2+}$ is 586; Analysis calc'd for [W$_3$(μ$_3$-O)$_2$(O$_2$CCHOHCH$_3$)$_6$(H$_2$O)$_3$]Cl$_2$, C$_{18}$H$_{36}$Cl$_2$O$_{23}$W$_3$: C, 17.30; H 2.92; Cl, 5.70; W, 44.38; found: C, 17.55; H, 3.39; Cl, 6.52; W, 46.61.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A compound of the general formula:

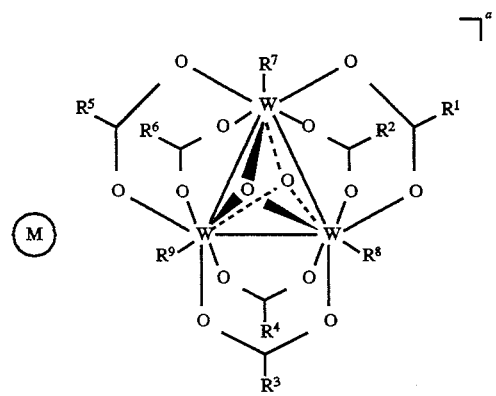

wherein R$^1$ is —C$_k$H$_l$Z$_m$ or —(C$_k$H$_l$Z$_n$) (C$_6$H$_{(5-q)}$ Z$_q$)$_p$; R$^2$ is —C$_k$H$_l$Z$_m$ or —(C$_k$H$_l$Z$_n$) (C$_6$H$_{(5-q)}$ Z$_q$)$_p$; R$^3$ is —C$_k$H$_l$Z$_m$ or —(C$_k$H$_l$Z$_n$) (C$_6$H$_{(5-q)}$ Z$_q$)$_p$; R$^4$ is —(C$_k$H$_l$Z$_m$) or —(C$_k$H$_l$Z$_n$) (C$_6$H$_{(5-q)}$ Z$_q$)$_p$; R$^5$ is —C$_k$H$_l$Z$_m$ or —(C$_k$H$_l$Z$_n$) (C$_6$H$_{(5-q)}$ Z$_q$)$_p$; R$^6$ is —C$_k$H$_l$Z$_m$ or —(C$_k$H$_l$Z$_n$) (C$_6$H$_{(5-q)}$ Z$_q$)$_p$; Z is a functional group attachable on aliphatic chains or aromatic rings; R$^7$ is an anionic molecule, —C$_k$H$_l$Z$_m$ or —(C$_k$H$_l$Z$_n$) (C$_6$H$_{(5-q)}$ Z$_q$)$_p$; R$^8$ is an anionic molecule, —C$_k$H$_l$Z$_m$ or —(C$_k$H$_l$Z$_n$) (C$_6$H$_{(5-q)}$ Z$_q$)$_p$; R$^9$ is an anionic molecule, —C$_k$H$_l$Z$_m$ or —(C$_k$H$_l$Z$_n$) (C$_6$H$_{(5-q)}$ Z$_q$)$_p$; k is about 0–20; l is about 0–50; m is about 1–50; n is about 0–50; p is about 1–10; q is about 1–5; M is a counter positive or negative ion; and a is about −6–+6.

2. The compound of claim 1 wherein $R^1$ is —$CH_2OCH_3$; $R^2$ is —$CH_2OCH_3$; $R^3$ is —$CH_2OCH_3$; $R^4$ is —$CH_2OCH_3$; $R^5$ is —$CH_2OCH_3$; $R^6$ is —$CH_2OCH_3$; $R^7$ is —$CH_2OCH_3$; $R^8$ is —$CH_2OCH_3$; $R^9$ is —$CH_2OCH_3$; M is sodium; and a is −1.

3. The compound of claim 1 wherein $R^1$ is —$CH_2OCH_3$; $R^2$ is —$CH_2OCH_3$; $R^3$ is —$CH_2OCH_3$; $R^4$ is —$CH_2OCH_3$; $R^5$ is —$CH_2OCH_3$; $R^6$ is —$CH_2OCH_3$; $R^7$ is $H_2O$; $R^8$ is $OH^-$; $R^9$ is $OH^-$; and a is 0.

4. The compound of claim 1 wherein $R^1$ is —$CH_2OCH_3$; $R^2$ is —$CH_2OCH_3$; $R^3$ is —$CH_2OCH_3$; $R^4$ is —$CH_2OCH_3$; $R^5$ is —$CH_2OCH_3$; $R^6$ is —$CH_2OCH_3$; $R^7$ is $H_2O$; $R^8$ is $H_2O$; $R^9$ is $OH^-$; M is $Cl^-$; and a is +1.

5. The compound of claim 1 wherein $R^1$ is —$CH_2OCH_3$; $R^2$ is —$CH_2OCH_3$; $R^3$ is —$CH_2OCH_3$; $R^4$ is —$CH_2OCH_3$; $R^5$ is —$CH_2OCH_3$; $R^6$ is —$CH_2OCH_3$; $R^7$ is $H_2O$; $R^8$ is $H_2O$; $R^9$ is $H_2O$; M is $Cl^-$; and a is +2.

6. The compound of claim 1 wherein $R^1$ is —$CH=CH_2$; $R^2$ is —$CH=CH_2$; $R^3$ is —$CH=CH_2$; $R^4$ is —$CH=CH_2$; $R^5$ is —$CH=CH_2$; $R^6$ is —$CH=CH_2$; $R^7$ is —$CH=CH_2$; $R^8$ is —$CH=CH_2$; $R^9$ is —$CH=CH_2$; M is $Na^+$; and a is −1.

7. The compound of claim 1 wherein $R^1$ is —$CH=CH_2$; $R^2$ is —$CH=CH_2$; $R^3$ is —$CH=CH_2$; $R^4$ is —$CH=CH_2$; $R^5$ is —$CH=CH_2$; $R^6$ is —$CH=CH_2$; $R^7$ is $H_2O$; $R^8$ is $H_2O$; $R^9$ is $H_2O$; M is $Cl^-$; and a is +2.

8. The compound of claim 1 wherein $R^1$ is —$CH_2C_6H_4OH$; $R^2$ is —$CH_2C_6H_4OH$; $R^3$ is —$CH_2C_6H_4OH$; $R^4$ is —$CH_2C_6H_4OH$; $R^5$ is —$CH_2C_6H_4OH$; $R^6$ is —$CH_2C_6H_4OH$; $R^7$ is —$CH_2C_6H_4OH$; $R^8$ is —$CH_2C_6H_4OH$; $R^9$ is —$CH_2C_6H_4OH$ M is sodium; and a is −1.

9. The compound of claim 1 wherein $R^1$ is —$CH_2C_6H_4OH$; $R^2$ is —$CH_2C_6H_4OH$; $R^3$ is —$CH_2C_6H_4OH$; $R^4$ is —$CH_2C_6H_4OH$; $R^5$ is —$CH_2C_6H_4OH$; $R^6$ is —$CH_2C_6H_4OH$; $R^7$ is $H_2O$; $R^8$ is $H_2O$; $R^9$ is $H_2O$; M is $Cl^-$; and a is +2.

10. The compound of claim 1 wherein $R^1$ is —$C(O)CH_3$; $R^2$ is —$C(O)CH_3$; $R^3$ is —$C(O)CH_3$; $R^4$ is —$C(O)CH_3$; $R^5$ is —$C(O)CH_3$; $R^6$ is —$C(O)CH_3$; $R^7$ is —$C(O)CH_3$; $R^8$ is —$C(O)CH_3$; $R^9$ is —$C(O)CH_3$; M is sodium; and a is −1.

11. The compound of claim 1 wherein $R^1$ is —$CH(OH)CH_3$; $R^1$ is —$CH(OH)CH_3$; $R^3$ is —$CH(OH)CH_3$; $R^4$ is —$CH(OH)CH_3$; $R^5$ is —$CH(OH\ CH_3$; $R^6$ is —$CH(OH)CH_3$; $R^7$ is —$CH(OH)CH_3$; $R^8$ is —$CH(OH)CH_3$; $R^9$ is —$CH(OH)CH_3$; M is sodium; and n is −1.

12. The compound of claim 1 wherein $R^1$ is —$CH(OH)CH_3$; $R^2$ is —$CH(OH)CH_3$; $R^3$ is —$CH(OH)CH_3$; $R^4$ is —$CH(OH)CH_3$; $R^5$ is —$CH(OH)CH_3$; $R^6$ is —$CH(OH)CH_3$; $R^7$ is $H_2O$; $R^8$ is $OH^-$; $R^9$ is $OH^-$; and a is 0.

13. The compound of claim 1 wherein $R^1$ is —$CH(OH)CH_3$; $R^2$ is —$CH(OH)CH_3$; $R^3$ is —$CH(OH)CH_3$; $R^4$ is —$CH(OH)CH_3$; $R^5$ is —$CH(OH)CH_3$; $R^6$ is —$CH(OH)CH_3$; $R^7$ is $H_2O$; $R^8$ is $H_2O$; $R^9$ is $OH^-$; M is $Cl^-$; and a is +1.

14. The compound of claim 1 wherein $R^1$ is —$CH(OH)CH_3$; $R^2$ is —$CH(OH)CH_3$; $R^3$ is —$CH(OH)CH_3$; $R^4$ is —$CH(OH)CH_3$; $R^5$ is —$CH(OH)CH_3$; $R^6$ is —$CH(OH)CH_3$; $R^7$ is $H_2O$; $R^8$ is $H_2O$; $R^9$ is $H_2O$; M is $Cl^-$; and a is +2.

15. A method of imaging comprising the administration of a diagnostically effective amount of a compound of the general formula:

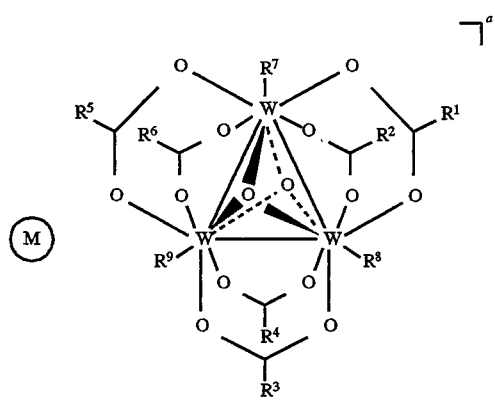

wherein $R^1$ is —$C_kH_lZ_m$ or —$(C_kH_lZ_n)$ $(C_6H_{(5-q)} Z_q)_p$; $R^2$ is —$C_kH_lZ_m$ or —$(C_kH_lZ_m)$ $(C_6H_{(5-q)} Z_q)_p$; $R^3$ is —$C_kH_lZ_m$ or —$(C_kH_lZ_n)$ $(C_6H_{(5-q)} Z_q)_p$; $R^4$ is —$(C_kH_lZ_m)$ or —$(C_kH_lZ_n)$ $(C_6H_{(5-q)} Z_q)_p$; $R^5$ is —$C_kH_lZ_m$ or —$(C_kH_lZ_n)$ $(C_6H_{(5-q)} Z_q)_p$; $R^6$ is —$C_kH_lZ_m$ or —$(C_kH_lZ_n)$ $(C_6H_{(5-q)} Z_q)_p$; Z is a functional group attachable on aliphatic chains or aromatic rings; $R^7$ is an anionic molecule, neutral molecule, —$C_kH_lZ_m$ or —$(C_kH_lZ_n)$ $(C_6H_{(5-q)} Z_q)_p$; $R^8$ is an anionic molecule, neutral molecule, —$C_kH_lZ_m$ or —$(C_kH_lZ_n)$ $(C_6H_{(5-q)} Z_q)_p$; $R^9$ is an anionic molecule, neutral molecule, —$C_kH_lZ_m$ or —$(C_kH_lZ_n)$ $(C_6H_{(5-q)} Z_q)_p$; k is about 0–20; l is about 0–50; m is about 1–50; n is about 0–50; p is about 1–10; q is about 1–5; M is a counter positive or negative ion; and a is about −6–+6.

16. The method of claim 15 wherein $R^1$ is —$CH_2OCH_3$; $R^2$ is —$CH_2OCH_3$; $R^3$ is —$CH_2OCH_3$; $R^4$ is —$CH_2OCH_3$; $R^5$ is —$CH_2OCH_3$; $R^6$ is —$CH_2OCH_3$; $R^7$ is —$CH_2OCH_3$; $R^8$ is —$CH_2OCH_3$; $R^9$ is —$CH_2OCH_3$; M is sodium; and a is −1.

17. The method of claim 15 wherein $R^1$ is —$CH_2OCH_3$; $R^2$ is —$CH_2OCH_3$; $R^3$ is —$CH_2OCH_3$; $R^4$ is —$CH_2OCH_3$; $R^5$ is —$CH_2OCH_3$; $R^6$ is —$CH_2OCH_3$; $R^7$ is $H_2O$; $R^8$ is $OH^-$; $R^9$ is $OH^-$; and a is 0.

18. The method of claim 15 wherein $R^1$ is —$CH_2OCH_3$; $R^2$ is —$CH_2OCH_3$; $R^3$ is —$CH_2OCH_3$; $R^4$ is —$CH_2OCH_3$; $R^5$ is —$CH_2OCH_3$; $R^6$ is —$CH_2OCH_3$; $R^7$ is $H_2O$; $R^8$ is $H_2O$; $R^9$ is $OH^-$; M is $Cl^-$; and a is +1.

19. The method of claim 15 wherein $R^1$ is —$CH_2OCH_3$; $R^2$ is —$CH_2OCH_3$; $R^3$ is —$CH_2OCH_3$; $R^4$ is —$CH_2OCH_3$; $R^5$ is —$CH_2OCH_3$; $R^6$ is —$CH_2OCH_3$; $R^7$ is $H_2O$; $R^8$ is $H_2O$; $R^9$ is $H_2O$; M is $Cl^-$; and a is +2.

20. The method of claim 15 wherein $R^1$ is —$CH=CH_2$; $R^2$ is —$CH=CH_2$; $R^3$ is —$CH=CH_2$; $R^4$ is —$CH=CH_2$; $R^5$ is —$CH=CH_2$; $R^6$ is —$CH=CH_2$; $R^7$ is —$CH=CH_2$; $R^8$ is —$CH=CH_2$; $R^9$ is —$CH=CH_2$; M is sodium and a is −1.

21. The method of claim 15 wherein $R^1$ is —$CH=CH_2$; $R^2$ is —$CH=CH_2$; $R^3$ is —$CH=CH_2$; $R^4$ is —$CH=CH_2$; $R^5$ is —$CH=CH_2$; $R^6$ is —$CH=CH_2$; $R^7$ is $H_2O$; $R^8$ is $H_2O$; $R^9$ is $H_2O$; M is $Cl^-$; and a is +2.

22. The method of claim 15 wherein $R^1$ is —$CH_2C_6H_4OH$; $R^2$ is —$CH_2C_6H_4OH$; $R^3$ is —$CH_2C_6H_4OH$; $R^4$ is —$CH_2C_6H_4OH$; $R^5$ is —$CH_2C_6H_4OH$; $R^6$ is —$CH_2C_6H_4OH$; $^7$ is —$CH_2C_6H_4OH$; $R^8$ is —$CH_2C_6H_4OH$; $R^9$ is —$CH_2C_6H_4OH$ M is sodium; and a is −1.

23. The method of claim 15 wherein $R^1$ is —$CH_2C_6H_4OH$; $R^2$ is —$CH_2C_6H_4OH$; $R^3$ is —$CH_2C_6H_4OH$; $R^4$ is —$CH_2C_6H_4OH$; $R^5$ is —$CH_2C_6H_4OH$; $R^6$ is —$CH_2C_6H_4OH$; $R^7$ is $H_2O$; $R^8$ is $H_2O$; $R^9$ is $H_2O$; M is $Cl^-$; and a is +2.

24. The method of claim 15 wherein $R^1$ is —C(O)CH$_3$; $R^2$ is —C(O)CH$_3$; $R^3$ is —C(O)CH$_3$; $R^4$ is —C(O)CH$_3$; $R^5$ is —C(O)CH$_3$; $R^6$ is —C(O)CH$_3$; $R^7$ is —C(O)CH$_3$; $R^8$ is —C(O)CH$_3$; $R^9$ is —C(O)CH$_3$; M is sodium; and a is −1.

25. The method of claim 15 wherein $R^1$ is —CH(OH)CH$_3$; $R^2$ is —CH(OH)CH$_3$; $R^3$ is —CH(OH)CH$_3$; $R^4$ is —CH(OH)CH$_3$; $R^5$ is —CH(OH)CH$_3$; $R^6$ is —CH(OH)CH$_3$; $R^7$ is —CH(OH)CH$_3$; $R^8$ is —CH(OH)CH$_3$; $R^9$ is —CH(OH)CH$_3$; M is sodium; and n is −1.

26. The method of claim 15 wherein $R^1$ is —CH(OH)CH$_3$; $R^2$ is —CH(OH)CH$_3$; $R^3$ is —CH(OH)CH$_3$; $R^4$ is —CH(OH)CH$_3$; $R^5$ is —CH(OH)CH$_3$; $R^6$ is —CH(OH)CH$_3$; $R^7$ is H$_2$O; $R^8$ is OH$^-$; $R^9$ is OH$^-$; and a is 0.

27. The method of claim 12 wherein $R^1$ is —CH(OH)CH$_3$; $R^2$ is —CH(OH)CH$_3$; $R^3$ is —CH(OH)CH$_3$; $R^4$ is —CH(OH)CH$_3$; $R^5$ is —CH(OH)CH$_3$; $R^6$ is —CH(OH)CH$_3$; $R^7$ is H$_2$O; $R^8$ is H$_2$O; $R^9$ is OH$^-$; M is Cl$^-$; and a is +1.

28. The method of claim 12 wherein $R^1$ is —CH(OH)CH$_3$; $R^2$ is —CH(OH)CH$_3$; $R^3$ is —CH(OH)CH$_3$; $R^4$ is —CH(OH)CH$_3$; $R^5$ is —CH(OH)CH$_3$; $R^6$ is —CH(OH)CH$_3$; $R^7$ is H$_2$O; $R^8$ is H$_2$O; $R^9$ is H$_2$O; M is Cl$^-$; and a is +2.

* * * * *